United States Patent [19]

Manz

[11] Patent Number: 5,250,263
[45] Date of Patent: Oct. 5, 1993

[54] APPARATUS FOR PROCESSING OR PREPARING LIQUID SAMPLES FOR CHEMICAL ANALYSIS

[75] Inventor: Andreas Manz, Basle, Switzerland

[73] Assignee: Ciba-Geigy Corporation, Ardsley, N.Y.

[21] Appl. No.: 785,134

[22] Filed: Oct. 30, 1991

[30] Foreign Application Priority Data

Nov. 1, 1990 [CH] Switzerland .................. 3467/90

[51] Int. Cl.$^5$ ............................................. G01N 33/00
[52] U.S. Cl. ......................................... 422/81; 422/63; 422/64; 422/68.1; 422/103; 436/52; 436/54
[58] Field of Search ................. 422/63, 64, 68.1, 81, 422/82, 103, 99; 436/52, 54

[56] References Cited

U.S. PATENT DOCUMENTS

| | | | |
|---|---|---|---|
| 3,404,780 | 10/1968 | Jungner | 422/63 X |
| 4,129,419 | 12/1978 | Hermann, Jr. | 422/64 |
| 4,254,084 | 3/1981 | Blum | 422/81 |
| 4,702,889 | 10/1987 | Cabrera et al. | 422/103 |
| 4,728,502 | 3/1988 | Hamill | 422/116 |
| 4,801,308 | 1/1989 | Keefer | 422/217 X |
| 4,948,565 | 8/1990 | Bemis et al. | 422/103 |
| 5,019,515 | 5/1991 | Gisin et al. | 436/52 |
| 5,087,425 | 2/1992 | Flossdorf et al. | 436/52 X |
| 5,137,698 | 8/1992 | Ansorge et al. | 422/116 X |

OTHER PUBLICATIONS

Bannwarth et al., "A System for Simultaneous Chemical Synthesis of Different DNA Fragments on Solid Support", DNA vol. 5, No. 5, 1986, pp. 413-419.
Chemical Engineer's Handbook—Perry, 1963, pp. 6-11, 6-12.

*Primary Examiner*—James C. Housel
*Assistant Examiner*—Maureen M. Wallenhorst
*Attorney, Agent, or Firm*—Luther A. R. Hall; Marla J. Mathias; William A. Teoli, Jr.

[57] ABSTRACT

An apparatus (1) for processing or preparing liquid samples for a preferably quantitative chemical analysis, especially for flow-injection analysis, is, for the purpose of miniaturisation and reducing the necessary sample volume while at the same time reducing the analysis time, assembled from a set of plate-like components (8). Each of the components (8) includes channels to form pipe pieces (9) and/or branches (13) with orifices and/or values, for example non-return valves, and/or pumps (6,7) in order to be able to feed the carrier liquid and sample to a detector (3) in the desired manner. Depending on the purpose of the analysis, the components (8) with the pipes and functional parts contained in them may be stacked in varying number and/or sequence and/or angular orientation relative to one another and can be connected in a sealing manner in the operative position.

13 Claims, 11 Drawing Sheets

APPARATUS FOR PROCESSING OR PREPARING LIQUID SAMPLES FOR CHEMICAL ANALYSIS

The invention relates to an apparatus for processing or preparing liquid samples for—preferably quantitative—chemical analysis, especially for flow-injection analysis (FIA), comprising feed channels or feed pipes leading to an analysis apparatus or a detector, there being provided at least one pipe for a carrier medium and at least one further pipe for feeding a sample to be investigated, which pipe leads into the feed pipe for the carrier medium and, if appropriate, comprises pumps, valves, mixing devices, other feed pipes for diluents for the samples, and the like.

Such an apparatus is known in various forms and has proved successful especially in flow-injection analysis. Depending on the type of detector, the evaluation unit connected thereto and the evaluation methods, data are obtained on the pH value, conductivity, spectral-photometric parameters, other physical or chemical parameters or also individual substances. In particular, the knowledge of such parameters also enables conclusions to be drawn regarding concentrations of the sample or in the sample. Flow-injection analysis, abbreviation FIA, meets, especially, the requirement for as small a sample volume as possible while at the same time achieving a high degree of accuracy and reproducibility of the analysis. The sample can be added to the carrier medium in portions in order to be transported by the latter to the detector. Refinements of that principle of procedure also make it possible first to dilute the sample and to add and mix in other reagents before the sample is injected or introduced into the carrier medium or to carry out additional reactions and analyses, for example chromatography or electrophoresis.

Flow analyses of that type, which, as far as possible, take place continuously, have a wide variety of uses. They can be used not only for examining water in connection with environmental protection but also for monitoring manufacturing processes. EP-A-243 310 describes, for example, a method of control and optimisation in the manufacture of textile processing agents and textile finishing agents and their intermediates using flow-injection analysis.

The particular disadvantage of those analyses is, however, the amount of space required to accommodate the individual components and aggregates, especially the mechanical components, such as, for example, the hitherto customary piston pumps, injection valves and the like. Those components and the feed pipes leading to them and the discharge pipes leading away from them use up a large amount of sample liquids and carrier liquids owing to their inherent volume and prolong transport times owing to the correspondingly long pipes.

The problem of the invention is accordingly considerably to reduce the analysis time even in the case of the operation of large installations having a large number of measuring sites and to reduce the amount of carrier liquid and reagents by at least one order of magnitude, preferably by from two to five orders of magnitude. In addition, easy construction of the apparatus is to be rendered possible.

The solution to that problem consists essentially in the fact that the apparatus can be assembled from a set of plate-like components to form a stack, and each of the components comprises pipe pieces and/or branches or orifices and/or valves, pumps or detectors.

Such plate-like components can be miniaturised relatively easily and permit an important development of the invention to the effect that the components can be stacked in varying number and/or sequence and/or orientation relative to one another to construct different flow systems and flow pipes and, in the operative position, are connected in a sealing manner. The flow systems so formed for flow-injection analysis have the same performance as conventional systems of that type. For example, in the case of an FIA system that is reduced in size by a factor of ten and is to scale, approximately 1000 times less of the reagents are consumed, but the analysis is nevertheless approximately ten times faster. In particular, sample-processing at the site where the sample is taken shortens transport paths. Thus, within such plate-like components, transport paths of, for example, only 5 mm can be obtained as against conventional pipes of up to 200 m in length. Electrical or optical signals can also be transmitted correspondingly faster.

One plate-like component in each case can comprise at least one functional part of the apparatus, for example a valve, a mixing chamber, a pump element, extractors, reactors, connecting pieces and/or detector cells, especially photo-optical or chromatographic detector cells or the like. Such functional parts can accordingly be incorporated and accommodated without difficulty at a required site within the stack of components.

The functional part provided on the plate-like component is advantageously arranged in the centre of that component, and feed and discharge channels or the like feedthrough openings can be arranged nearer to the edge or the periphery of the component. That has the advantage that the feed pipes especially can be brought in without difficulty and feed and discharge members can be readily accommodated without causing any complications with intersections. It is also, as a result, readily possible to modify the arrangement of the feed pipes, while maintaining the arrangement of the functional part, by a rotated arrangement of other components. That makes it easier to satisfy the most varied requirements for such apparatuses in spite of having only a relatively small number of components.

The connection of the apparatus to a control device can be effected in a simple manner via electrical cables, especially in the case of a detector, a pump and/or valves, via hydraulic and/or pneumatic hoses, for example in the case of pumps or valves, or via feed hoses for reagents, and via optical fibres, especially to a detector operating on the principle of transillumination with light. AU this is rendered possible by the stacking according to the invention of plate-like components having corresponding openings and channel sections, so that the entire apparatus may be in such a form that it is very space-saving and has a small inherent volume.

It is advantageously possible to arrange at least one pump inside the component(s) and/or outside the apparatus. The pump to be provided inside an assembly of components can be formed, for example, by a diaphragm arranged between two components, which diaphragm can be deflected from one side by means of pressure and/or reduced pressure and has suction and pressure pipes on its other side. By means of some of the components and the channels provided therein, such a diaphragm can accordingly be caused to oscillate by being deflected alternately in one direction by pressure and in the opposite direction by reduced pressure. Such an oscillating diaphragm can, on the other hand, on the opposite side remote from that deflecting mechanism, carry out the necessary pumping operations. Only a very small volume is required since a mechanical drive is not necessary.

In order to stack the individual components in varying sequence and/or angular position relative to one another, it is advantageous for the individual components to comprise centring or connecting holes or recesses at coinciding sites and for each component to comprise along its periphery several, for example four, centring or connecting holes for securing means which are offset with respect to one another by identical angles and are arranged at identical distances from the centre of the component. Several such connecting holes have the advantage that the connecting means extending through them can exert a uniform compressive force on the individual plate-like or wafer-like components so that the latter rest on one another in a sealing manner in the operative position.

The outer contours of the components may be identical and of equal size so that the components coincide. That improves stackability and the possibility of miniaturisation.

For example, the outer contour of the components may be circular or square. That facilitates the association of individual components, even at differing angular positions relative to one another, without losing the coincidence. However, other regular polygons, for example hexagons, are of course also possible shapes for the components in order to obtain the above-mentioned advantage.

An advantageous embodiment of the invention can provide that the plate-like components are glass, plastics or metal wafers, especially of refined steel. Such components are easy and inexpensive to manufacture. Useful results are possible, for example, with wafers the diameter of which is approximately 5 cm, but it is also possible to use any other size.

Further miniaturisation can be achieved when the plate-like components are chip-like wafers separated from a crystal. Such wafers can, for example, have a side measurement of from 2 to 20 mm. The flow openings, flow channels and/or connecting holes and/or recesses for functional parts can be etched into the components. It is known that extremely small openings and configurations of channel sections and the like can be produced with the etching technique, so that the desired miniaturisation with the resulting advantageous reduction in the necessary sample volume can be achieved to a high degree.

The mutually opposing surfaces of the plate-like components are plane-parallel and so even that, in the layered and connected operative position, they seal the edges of the flow openings or the like or seal at the surface of channel sections that are open at one side or also seal openings of functional parts. That facilitates the stacking and the assembly of the individual components because no special seals are required. It is, however, also possible to insert into the stack one or other of the wafers or one or other of the plate-like components as an additional sealing member, for example in the region of a pump or a valve.

In order to form a valve, a flow opening extending through a component may be funnel-shaped across the thickness of the component, at least in regions, and may contain a spherical valve member in the section tapering in the form of a funnel. If that region is acted upon by excess pressure, the bail can block the flow in the manner of a non-return valve. If, however, the direction of pressure is reversed, the valve can be opened.

For pressing the stacked plate-like components together in a sealing manner, threaded rods or screws that extend through the connecting holes may be provided.

Finally, the assembly of components may also comprise closing wafers having connections to the flow channels, which wafers may, if necessary, have a greater thickness and also a greater outside measurement so that conventional hoses can be adapted to the miniaturised flow channels.

Especially when the above-described features and measures are combined individually or collectively, an apparatus is obtained with which, depending on requirements, it is possible to carry out, in the smallest of spaces, flow-injection analyses for which very little of the reagents is required and which can nevertheless be carried out very rapidly without impairing accuracy. Since the space required by an apparatus is also very small, the apparatus can in many cases be accommodated as close as possible to the site where such analysis is required, whether in connection with environmental protection or for monitoring manufacturing processes or the like.

The invention together with its essential details is described in more detail hereinafter in several embodiments with reference to the drawings.

In a diagrammatic and enlarged view.

In the embodiments described hereinafter, corresponding components, even if they are in differing forms, have identical reference numerals; in particular, the various embodiments of an apparatus for processing or preparing liquid samples for chemical analysis each have the reference numeral 1.

Figure 1:
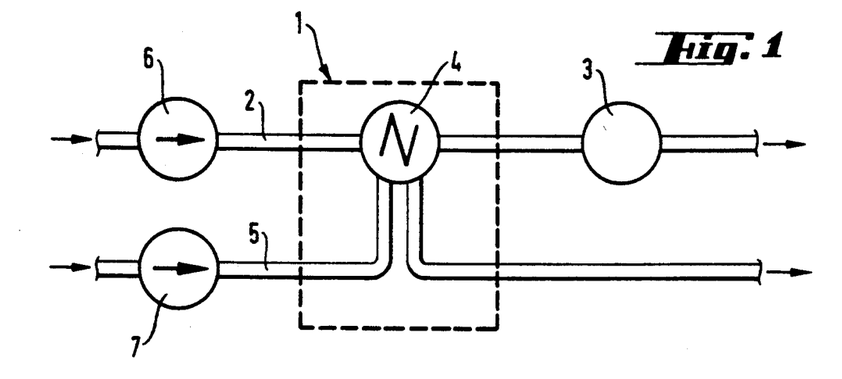
FIG. 1 shows a flow diagram of a simple example of a flow-injection analysis application with a pump for carrier liquid, a pump for a sample, an injection valve in the carrier liquid pipe, and a detector.

FIG. 1 shows a simple example of a flow-injection analysis application in which the apparatus 1 for processing the liquid sample comprises essentially a feed pipe 2 to a detector 3, an injection valve 4 and a feed pipe 5 to that injection valve 4. This arrangement is shown as a circuit diagram in FIG. 1, there being arranged at the beginning of the feed pipes 2 and 5 a pump 6 and 7, respectively, which, in many of the following embodiments, can be integrated inside the apparatus 1 or alternatively, according to FIG. 7, arranged outside the apparatus 1.

Both that very simply constructed apparatus 1 according to FIG. 1 and the apparatuses 1 of the same type described hereinafter having a greater number of individual pipe sections or functional parts can, in accordance with FIGS. 2 to 5 and 9 to 16, be assembled from a stack of plate-like components 8. The components 8 differ from one another in their construction in respect of pipe parts 9, flow openings 10, valves 11 or central chambers 12. Nevertheless, hereinafter all of the components have the reference numeral "8" since, within an assembly of components of an apparatus 1, they have identical outer contours and can be stacked on one another so that they coincide.

The very simple construction according to FIGS. 1 to 5 already shows that the components 8 each comprise pipe pieces 9 and branches 13 and also flow openings 10 in order to bring together the pipes 2 and 5 at an injection site with an internal volume corresponding to the injection valve 4, after which the pipe 5 leads away again while the pipe 2 can lead further to an external detector. Even with this embodiment, therefore, quite a considerable amount of space and internal volume is saved in the apparatus 1 according to FIG. 1 as a result of using stackable components 8, so that a correspondingly small amount of sample fluid and a correspondingly small amount of carrier fluid are required for the actual analysis.

Figure 6:
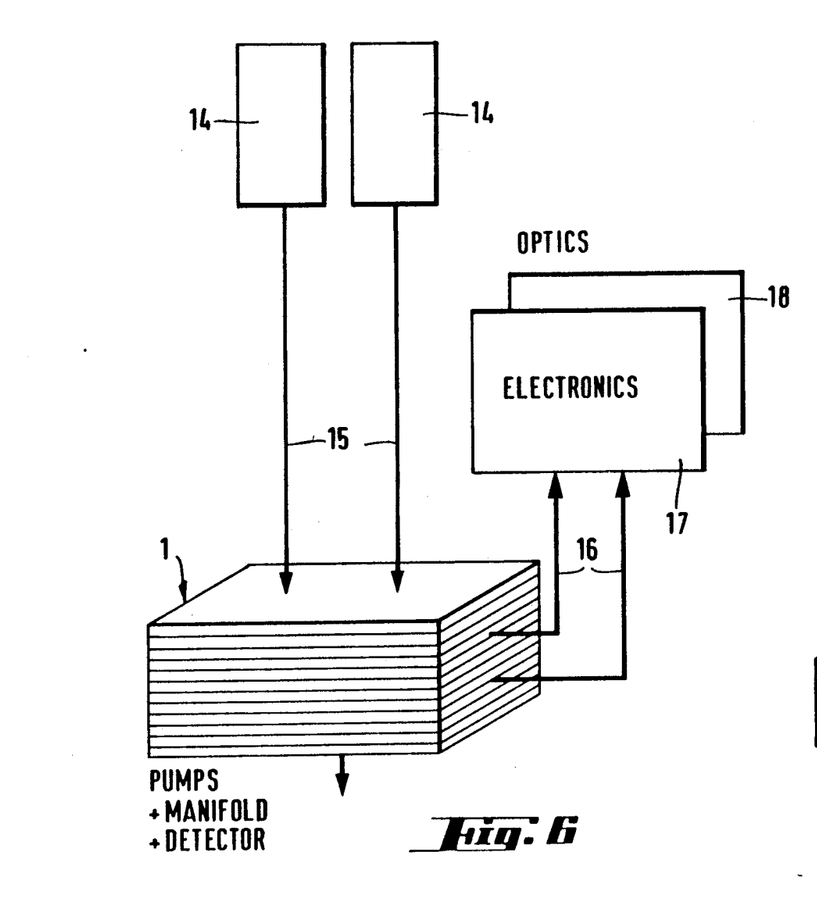
FIG. 6 shows an apparatus according to the invention in a diagrammatic view in which, outside the stack of components having an internal pump, pipe members and a detector, supply containers and signal evaluation units are indicated diagammatically.
Figure 7:
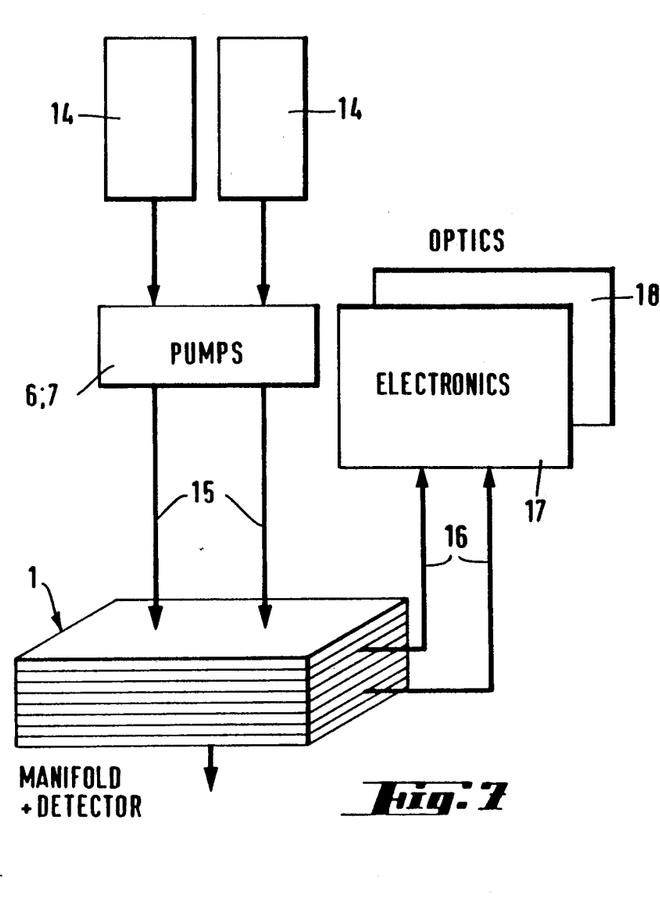
FIG. 7 shows an arrangement corresponding to FIG. 6 in which the pumps are also provided outside the stack of components.

In FIGS. 6 and 7, the apparatuses 1, which are each assembled from stackable components 8 having different functions, are shown merely as blocks. It can be seen that it is possible to provide outside the actual apparatus 1 supply containers 14 which are connected via conventional hoses or pipes 15 to the apparatuses 1, it being provided in FIG. 6 that pumps 6 and 7 are arranged inside the apparatus 1 in a manner to be described later, whereas, in the solution according to FIG. 7, they are in the form of external pumps.

FIGS. 6 and 7 also show connections, for example in the form of electrical cables 16, by means of which the apparatuses 1 can be connected to electronic signal evaluation units 17 or optical signal evaluation units 18.

Figure 8:
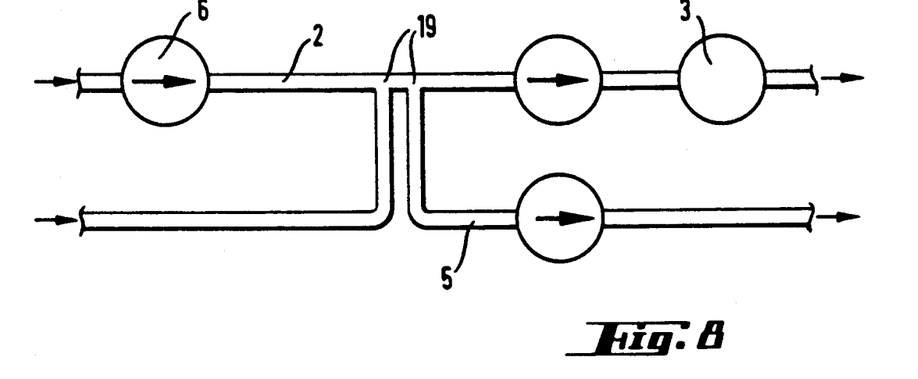
FIG. 8 shows, for the purpose of comparison, the arrangement according to FIG. 1 with conventional injection, and an externally controlled valve-free solution of such an injection with two T-pieces arranged next to one another, FIG. 9 a-d shows four different stackable components of an assembly of components according to the invention having ducts (a), a channel section (b), a central mixing chamber (c) and a channel system for injection (d), it also being possible for a plurality of each of these different individual components to be provided.
Figure 9A:
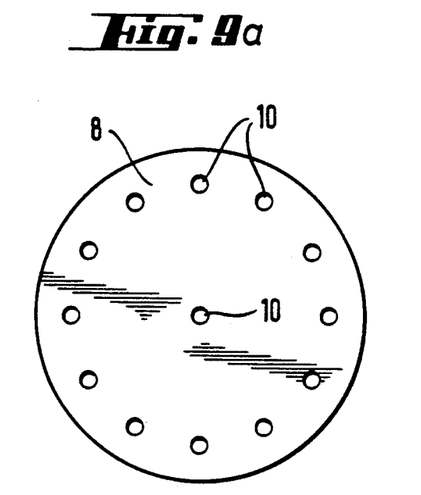
Figure 9B:
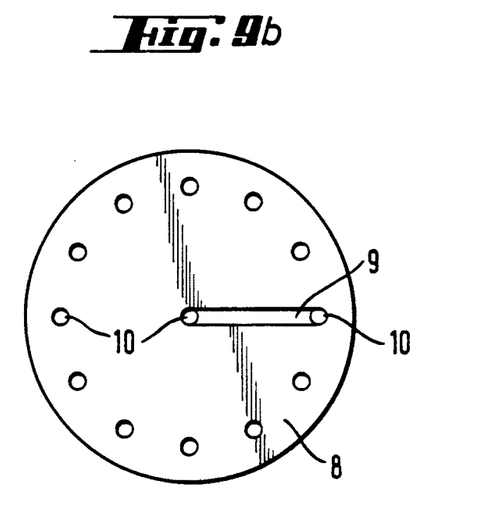
Figure 9C:
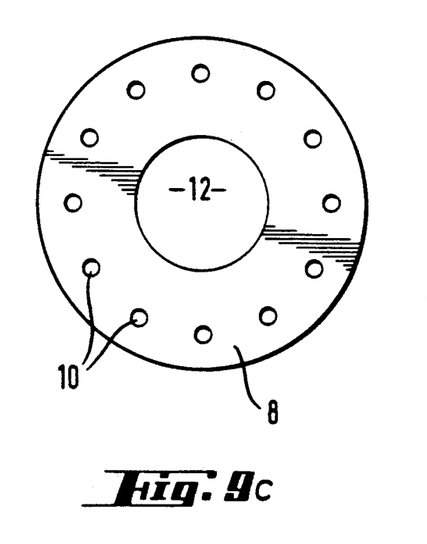
Figure 9D:
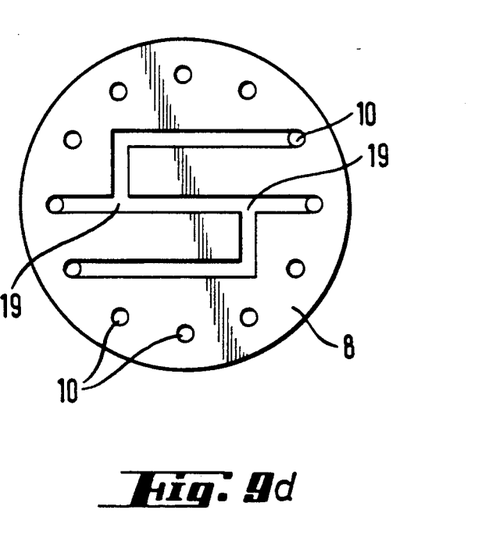

In FIG. 8, the apparatus 1 according to FIG. 1 having an injection valve 4 is shown in comparison with a flow diagram of such an apparatus 1 having two T-pieces 19 arranged in series, a pump being present at the pipe 2 both upstream and downstream of those T-pieces 19, while, in addition, a suction pump is also present at the branch pipe 5 downstream of the second T-piece so that, by actuating all those pumps, the desired injection from the pipe 5 into the pipe 2 can be effected.

The plate-like components 8 required therefor are shown in FIGS. 9 a-d, in which one component 8 comprises only flow openings 10, a further component 8 comprises a channel or a pipe piece 9, a further component comprises a central hole as a mixing chamber 12 and, especially, a final component 8 comprises a channel system having two T-pieces 19 arranged next to one another.

Figure 10:
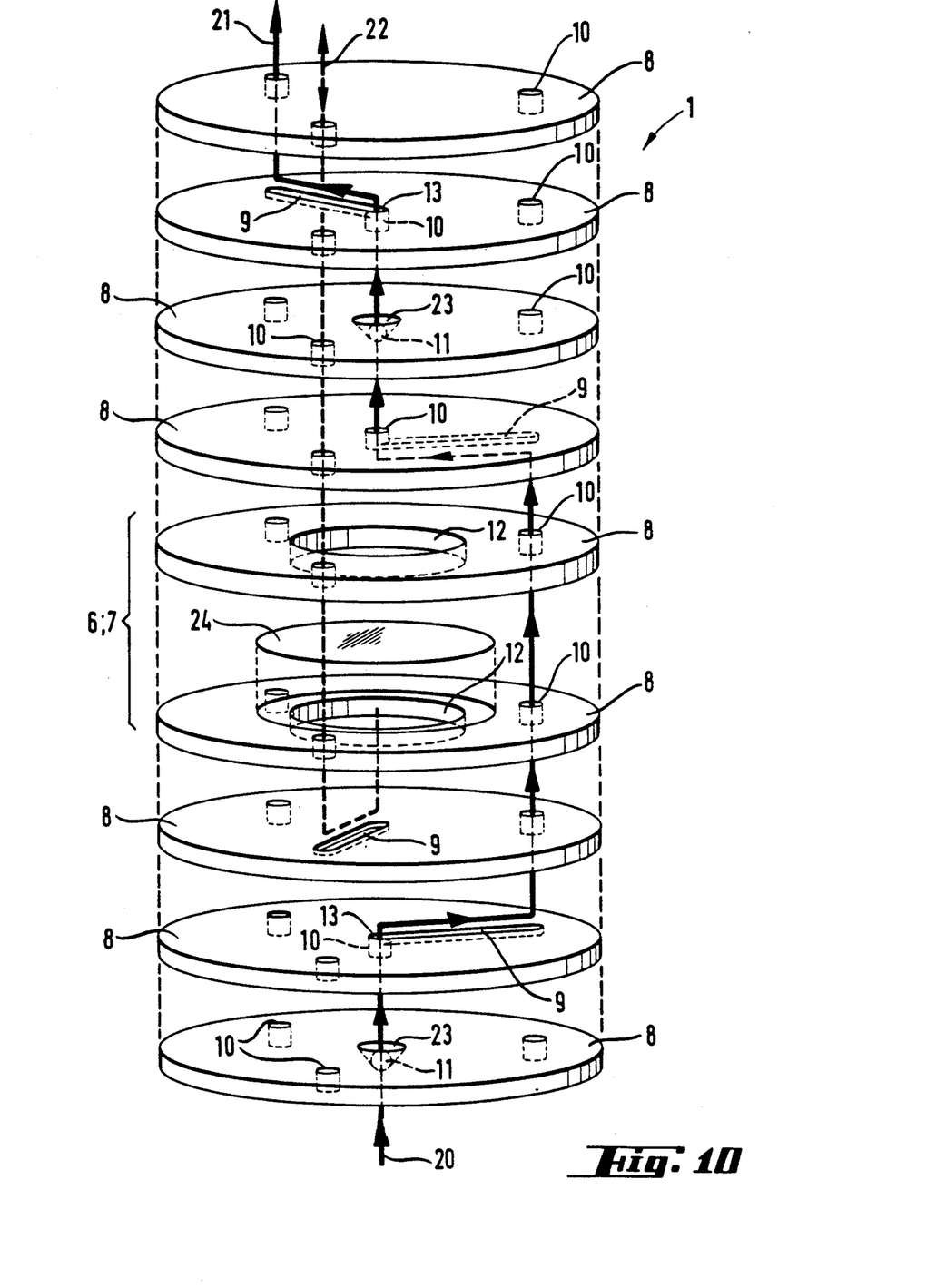
FIG. 10 shows an exploded view of a stack of different components having ducts, connecting channels, a non-return valve, and a pump which is formed by a flexible diaphragm and on both sides of which are provided plates having corresponding holes as mixing chambers or the like, FIG. 11 shows the assembly of components according to FIG. 10 in the assembled state between two closing plates having connections.
Figure 11:
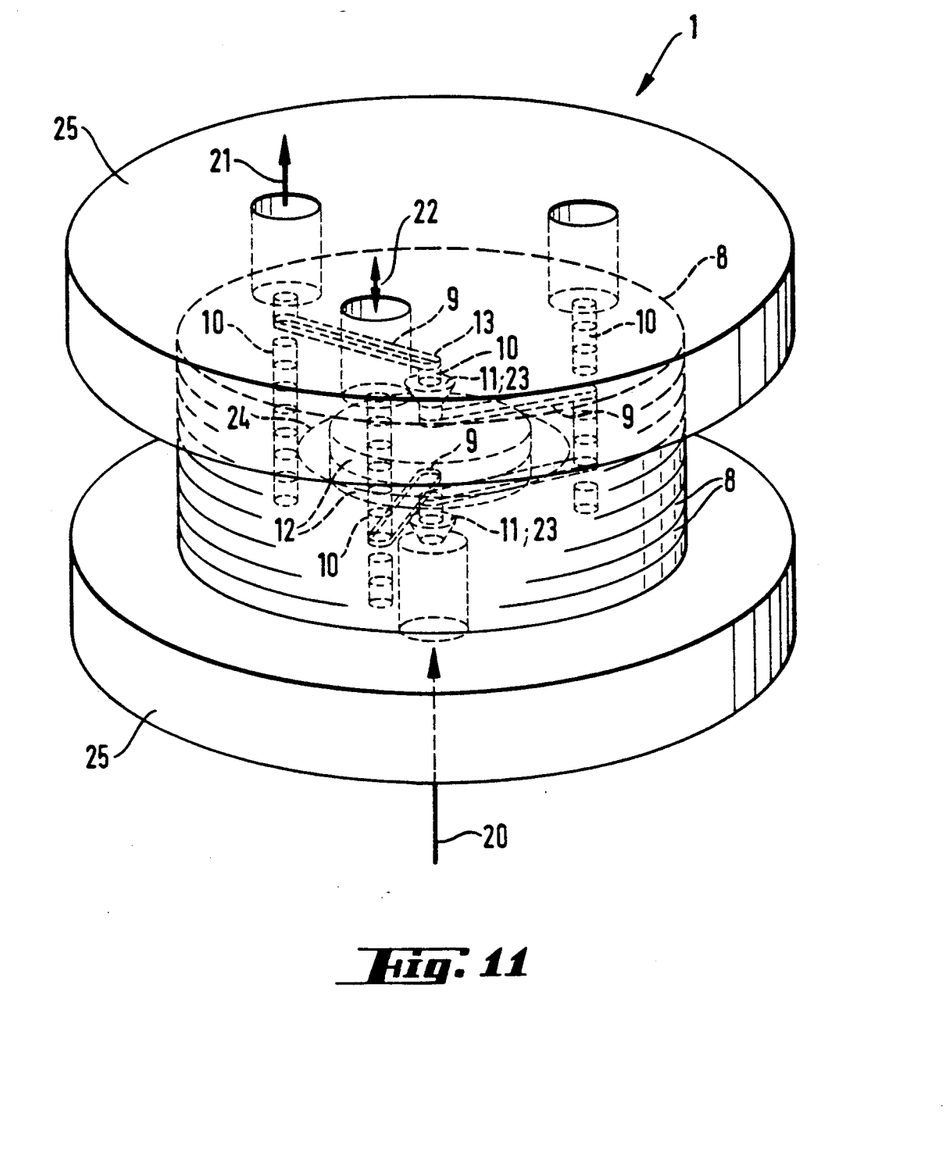

FIGS. 10 and 11 show an apparatus 1 in which a total of nine plate-like components 8 have been stacked to form an apparatus 1. FIG. 10 shows that, in a specific sequence, components 8 comprise flow openings 10, valves 11, chambers 12 and also branches 13 and pipe parts 9 to provide a passage from a lower inlet 26 to an outlet 21.

Two components having central chambers 12 are provided approximately in the middle of the stack of components 8 according to FIGS. 10 and 11. If a flexible diaphragm 24 is inserted between those components 8 it can be used as a pump 6 or 7 in that it is deflected from one side by means of pressure or reduced pressure so that on its other side it can exert a corresponding pump action on the chambers 12 as a result of the deflection. FIG. 10 indicates by a broken line the pressure pipe 22 serving to move such a diaphragm, the pressure pipe 22 leading likewise by way of flow openings 10 and pipe parts 9 at the corresponding components 8 to the operating chamber 12 below the flexible diaphragm.

It can also be seen, for example in the lowermost component 8 or in the third component from the top (in FIG. 10) that, in order to form a valve, a flow opening 23 extending through a component is funnel-shaped across the thickness of the component 8, in least in regions, and can contain a spherical valve member in its tapering section, although, owing to the smallness of the Figure, this is only shown schematically. Accordingly, the flow can take place in only one direction, that is to say, such a component can comprise a non-return valve, thereby ensuring that the pump formed by a flexible diaphragm 24 between two chambers 12 acts in the desired direction of transport. Nevertheless, no additional hoses and functional parts requiring a large amount of space are necessary; rather, it is possible to arrange those functions inside the assembly of components of the apparatus 1 at or between plate-like components 8 in a very space-saving manner. FIG. 11 gives an idea of how small the total outside measurement of the apparatus 1 is when the individual plate-like components 8 are connected securely in the form of a coherent stack, the assembly of components also comprising closing wafers 25 having connections as inlet 20 and outlet 21 to the flow channels of the apparatus 1. Such closing wafers are also shown in the embodiments according to FIGS. 12 and 13.

Figure 12:
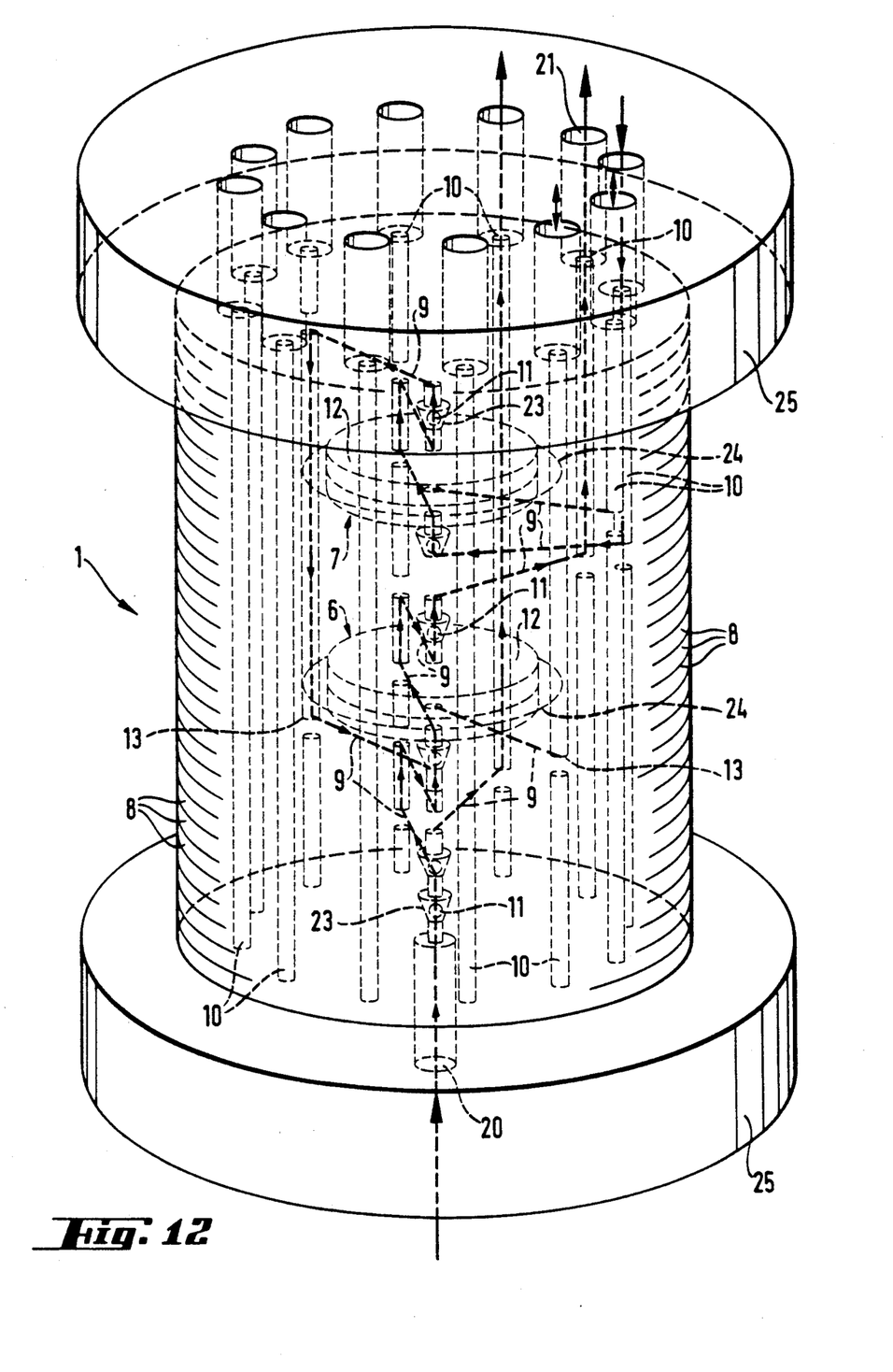
FIG. 12 shows an embodiment in the assembled state in which, for the sake of clarity, the individual plates are not shown individually, both a pump for carrier liquid and a pump for the sample being provided.

FIG. 12 shows an embodiment in which, in the manner described above, two pumps, namely a pump 6 for carrier liquid and a pump 7 for the sample, are accommodated inside an apparatus 1 composed of stacked plate-like components, each of those pumps 6 and 7 in turn being formed by two plates having chambers 12 and a diaphragm arranged between them. Correspondingly more inlets and outlets for pump control and pump operation are provided at the upper closing wafer 25. Nevertheless, even in the case of this extended apparatus 1 according to FIG. 12, there is a very small overall space requirement inside the stack of components 8 with a correspondingly small total internal volume.

Figure 13:
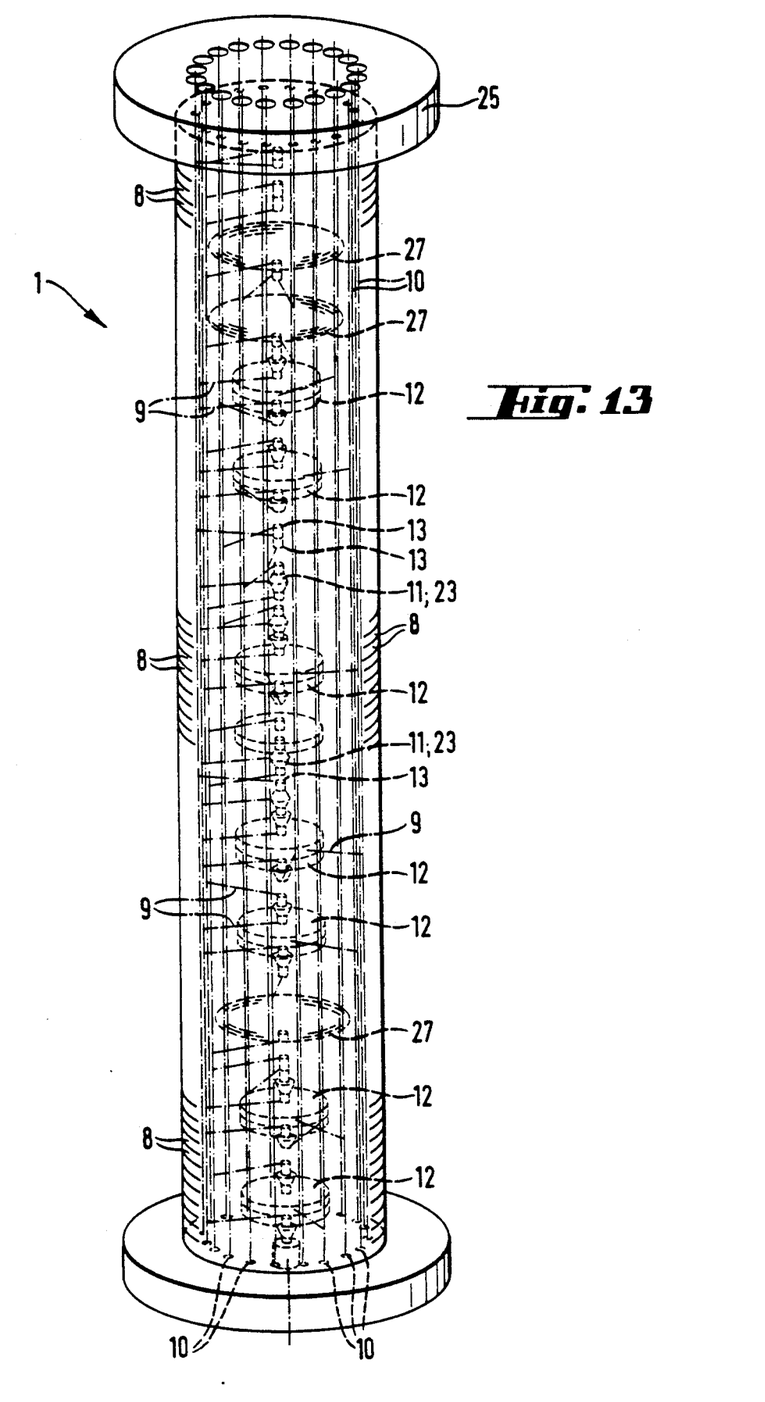
FIG. 13 shows a further embodiment of an apparatus assembled from stackable components of circular outer contour and having even more pipe sections, valves and pumps, suitable for an on-line glucose analysis, FIG. 14 a-h shows an assembly of components comprising a plurality of square chip-like plate-like components having different holes, channel sections or systems or mixing chambers.
Figure 14A:
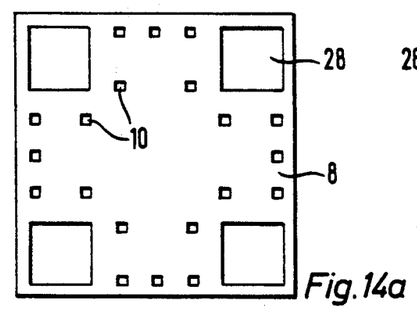
Figure 14B:
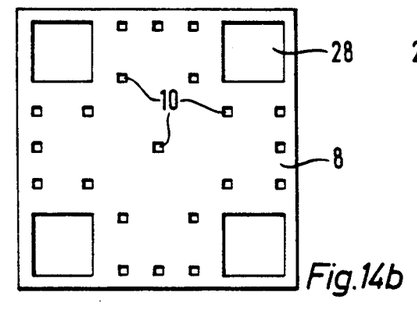
Figure 14C:
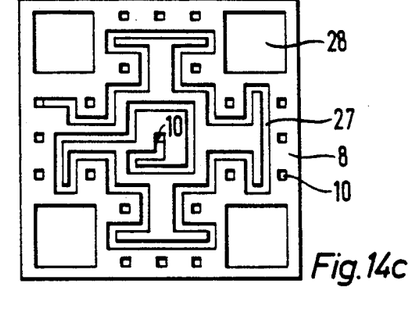
Figure 14D:
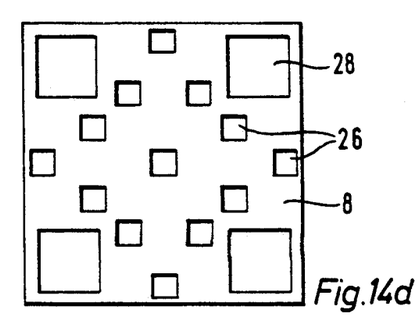
Figure 14E:
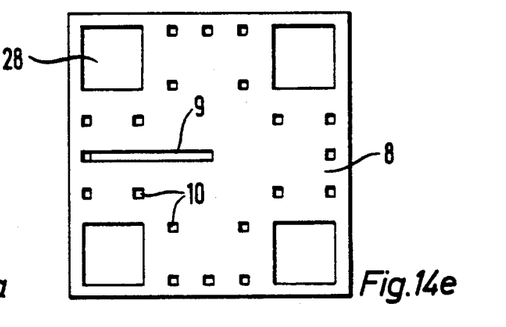
Figure 14F:
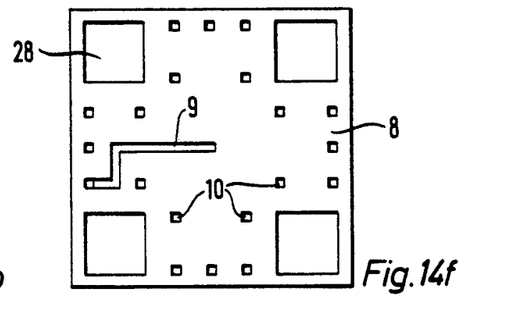
Figure 14G:
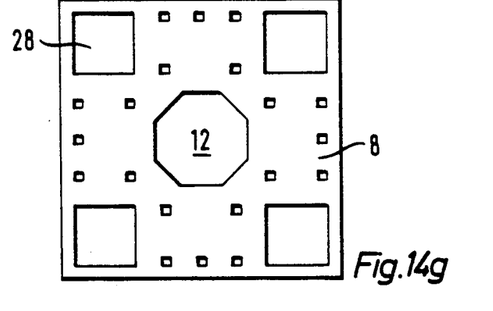
Figure 14H:
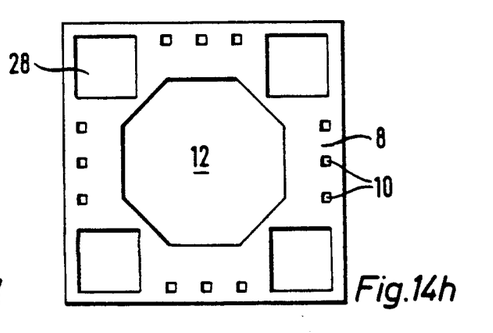

FIG. 13 shows that the number of plate-like components 8 having different functional parts can be further increased in order to construct, for example, a glucose analyser in the manner according to the invention.

More than one of some of the components 8 are present and, in particular, it is possible to use several components 8 having peripheral flow openings 10 since they can be rotated in such a manner with respect to one another, depending on the course of the complete pipe, that they can produce the corresponding connections to pipe parts 9 in parallel components 8, so that, overall, a continuous train of pipes is formed from the inlet 20 to the outlet 21 as has already been produced in FIG. 12 in a slightly simpler version of an apparatus 1.

Figures 2, 3:
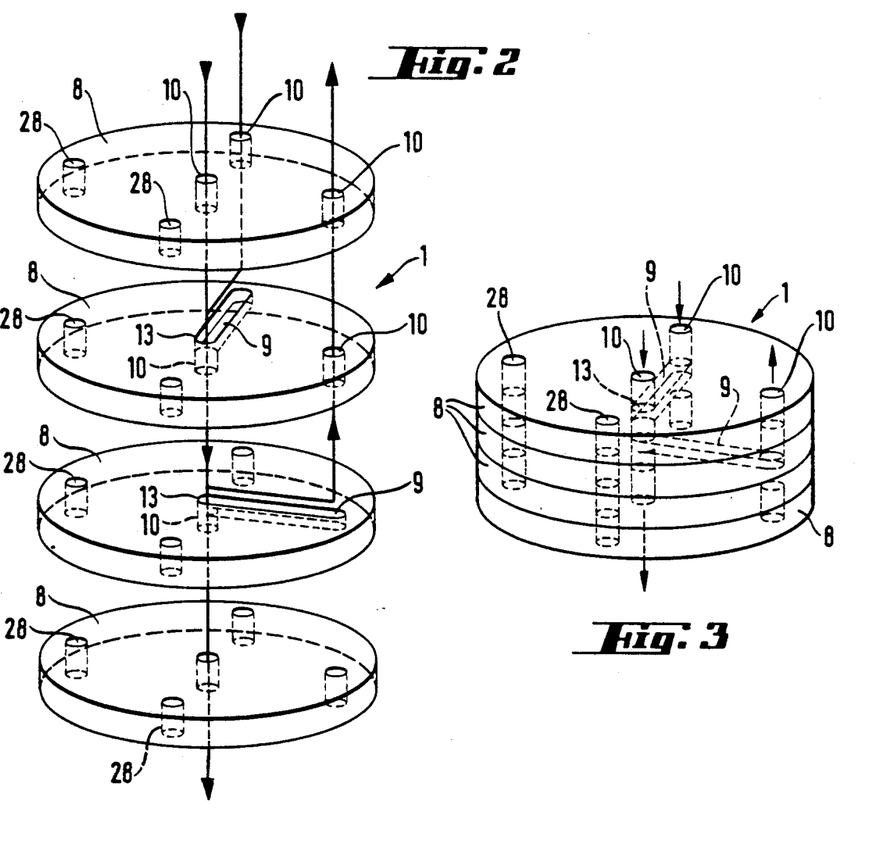
FIG. 2 shows an assembly of components according to the invention for producing the region bordered by a broken line in FIG. 1, that is to say, the injection valve with the feed and discharge pipes.
FIG. 3 shows the assembly of components according to FIG. 2 in stacked and assembled form.
Figure 4:
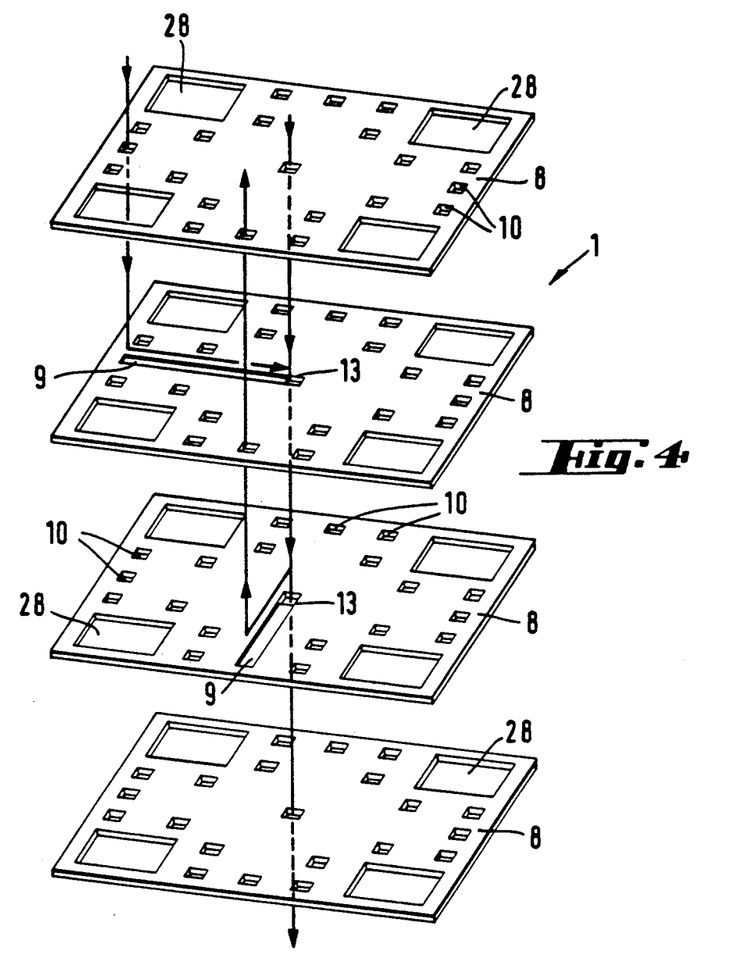
FIG. 4 shows a modified assembly of components in which the individual components are in the form of scaled-down chips having etched-in openings and are shown in their association with respect to one another.
Figure 5:
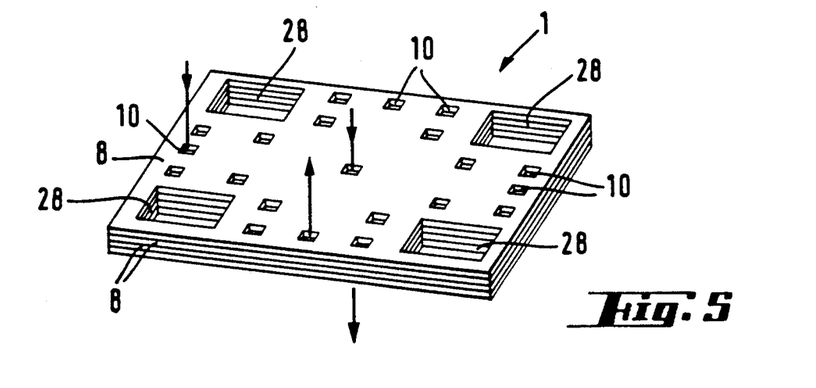
FIG. 5 shows the assembly of components according to FIG. 4 in assembled and stacked form.

While in the embodiments according to FIGS. 2, 3 and 9 a–d to 13 the plate-like components 8 have a circular outer contour and are, for example, glass, plastics or metal wafers having a diameter of approximately 50 mm or more, the embodiments according to FIGS. 4 and 5 and also 14 a–h to 16 show plate-like components 8 that can be used and assembled in an analogous manner and that are wafers separated in chip-like manner from a crystal and can accordingly have an even smaller outside measurement because the holes, channel sections and the like present in them can be provided by the etching process. In the embodiment, those components 8 have a square outer contour.

Especially in the example of an assembly of components shown in FIG. 14 a–h, more than one of each of the individual parts of which may be present, there can again be seen pipe parts 9, flow openings 10 or chambers 12, of different sizes, which may be mixing chambers or also pump elements. It is also indicated in the component 8 shown in FIG. 14d that adapters 26 can be provided for supporting glass capillaries with which the feeding of samples and the like can be carried out. Also shown in the component 8 of FIG. 14c are spiral channels 27 which can be accommodated on a very small component, even in very narrow turns, using the etching technique already mentioned, that is to say, they provide the possibility of achieving a mixing effect in the narrowest of spaces by means of numerous bends and turns. FIG. 13 also shows spiral channels 27 of that type.

Figure 15:
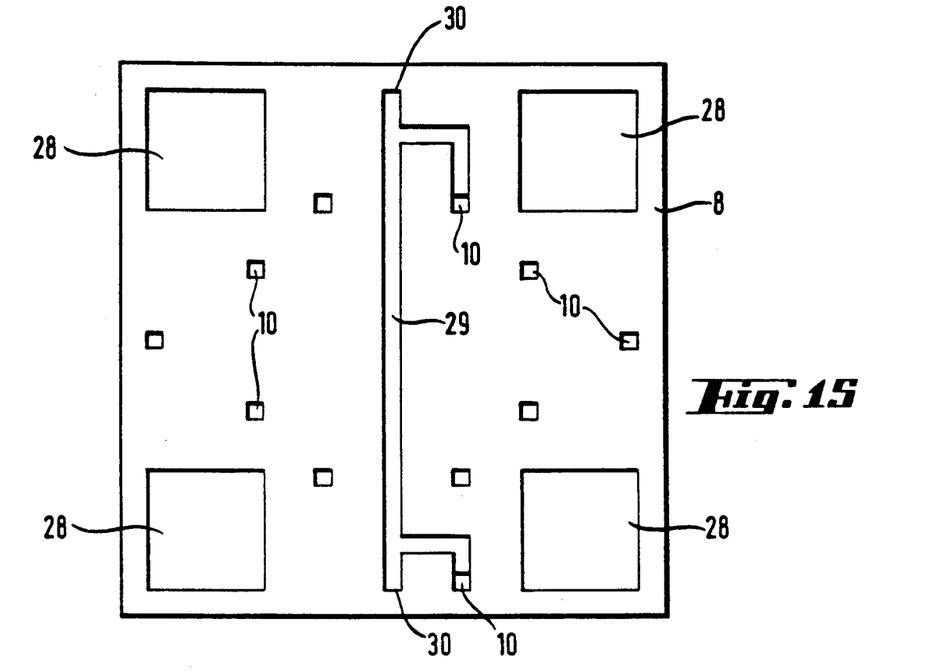
FIG. 15 shows a component that is suitable as an optical detector and has one inlet and one outlet to a channel section, delimited on both sides by reflective surfaces, for optical investigation.
Figure 16:
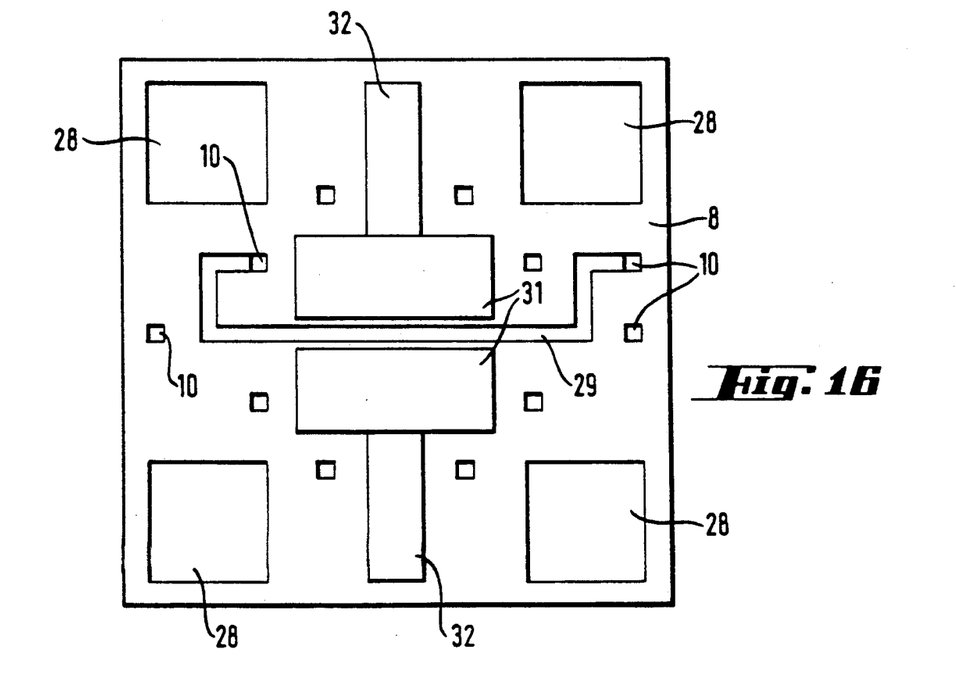
FIG. 16 shows a detector component for an electrochemical analysis having an ion-selective field effect transistor on both sides of a channel section used for electrochemical investigation.

In the case of all those components 8 in FIG. 14 and likewise in the case of the components 8 of FIGS. 15 and 16 which are shown on an enlarged scale in comparison, it is possible to see, in all four corners, positioning holes 28 which may also be present in the round wafers and which ensure that the stacked components are fixed in the correct position but also permit an arrangement of the components in a position in which they are rotated with respect to one another.

FIG. 15 shows a component 8 that comprises an inlet and an outlet to a channel section 29 which has reflective surfaces at both of its ends 30 in order thus to form an optical detector cell.

In FIG. 16 there is arranged on both sides of a comparable channel section 29, in turn comprising an inlet and an outlet, an ion-selective field effect transistor 31 by means of which the component 8 is converted into an electrochemical detector cell. The connections 32 of that transistor 31, like the transistor itself, can be readily attached in the known manner of construction for semiconductors.

Since the mutually opposing surfaces of the plate-like components 8 are each plane-parallel and even, in the layered and connected operative position they can seal the edges of the flow openings 10 or also of channels or channel sections 29, 27 or 9, as well as the chambers 12. By stacking, therefore, an apparatus 1 is produced in which the individual pipe regions and functional parts are sealed and do not require additional seals. For pressing the stacked plate-like components 8 together in a sealing manner, threaded rods or screws extending through the connecting or positioning holes 28 can be provided in a manner not shown in detail.

Apparatuses 1 having an extremely small outside measurement are thus produced that nevertheless comprise all the elements necessary to enable a flow-injection analysis to be prepared and carried out, only very small amounts of carrier liquid and sample being required owing to the miniaturisation, and the speed of analysis being considerably increased owing to the fact that the flow distances have been shortened. The apparatus 1 for processing or preparing liquid samples for a preferably quantitative chemical analysis, especially for flow-injection analysis, is, for the purpose of miniaturisation and reducing the necessary sample volume while at the same time reducing the analysis time, assembled from a set of plate-like components 8 to form a stack, each of the components 8 comprising pipe pieces 9 and/or branches 13 and/or orifices and/or valves, for example non-return valves, and/or pumps 6, 7, in order to be able to feed the carrier liquid and sample to a detector 3 in the desired manner. Depending on the purpose of the analysis, the components 8 with the pipes and functional parts contained in them may be stackable in varying number and/or sequence and/or angular orientation relative to one another and can be connected in a sealing manner in the operative position.

What is claimed is:

1. An apparatus for processing or preparing liquid samples for chemical analysis, especially for flow injection analysis (FIA), comprising in combination a plurality of plate components, said plate components each being provided with a central throughhole and several additional throughholes that are distributed across the surface of each plate component, at least one of said components having a horizontally extending channel segment in the form of a groove that extends from said central throughhole towards the periphery of the respective plate component, said plate components being stackable in a predetermined order of arrangement one above the other such that said central throughhole and at least some of the throughholes distributed across each plate component are in alignment with respective throughholes of neighboring components, thus forming at least one interconnected fluid channel system, which extends vertically through the stacked components and includes said horizontally extending channel segment provided in said at least one of said plate components, the channel system being adapted for transportation of a fluid through the stacked plate components; and further comprising at least one integrally formed diaphragm pump, consisting essentially of two of said neighboring plate components which enclose a diaphragm arranged between them, and activation means for deflecting the diaphragm vertically between a first and second position such that the diaphragm pump sucks or pumps fluid through respective throughholes which are provided in one of said two neighboring plate components located next to one side of said diaphragm, and which communicate with said at least one fluid channel system.

2. An apparatus according to claim 1, wherein the throughholes which are provided in said plate component next to one side of said diaphragm and through which said fluid is sucked or pumped are shaped as valves, said throughholes being funnel-shaped across the thickness of said component, and containing a vertically displaceable spherical valve member in a tapered region of said throughholes.

3. An apparatus according to claim 2, wherein assemblies of varying numbers of said plate components are stackable in varying sequences and orientations, each different assembly of said plate components defining a different channel system.

4. An apparatus according to claim 3, wherein in each channel system, there are provided a number of valves, each valve being defined by a throughhole in a respective plate component, said throughhole being funnel-shaped across the thickness of said component and containing a vertically displaceable spherical valve member in a tapered region of said throughhole.

5. An apparatus according to claim 1, wherein said plate components further comprise centering or connecting holes which are provided at their periphery such that, irrespective of an angular orientation of said plate components with respect to each other in a stacked combination said centering or connecting holes are in alignment with each other.

6. An apparatus according to claim 5, wherein said plate components have identical outer contours and are of equal size, such that when the components are stacked and the centering or connecting holes are in alignment, the circumferences of the components align.

7. An apparatus according to claim 6, wherein the outer contours of said plate components are circular or square.

8. An apparatus according to claim 1, wherein neighboring plate components have mutually opposing surfaces which have parallel planes such that upon assembly, said neighboring plate components engage sealingly so that no fluid can exit at the interface between said mutually opposing surfaces.

9. An apparatus according to claim 5, further comprising threaded rods or screws which extend through said centering or connecting holes for pressing said stacked plate components together in a sealing manner.

10. An apparatus according to claim 9, wherein said stacked plate components are arranged between two cover-plates, said cover plates having meeting surfaces which have parallel planes respective to the top-most and lower-most faces of the outer plate components of the stack, said cover-plates being provided with openings which communicate with said channel system, said openings being shaped to accommodate entry and exit lines for a sample, and including reflective surfaces for forming an optical detector cell.

11. An apparatus according to claim 1, wherein said activation means consists of electrical or hydraulic drive means for deflecting said diaphragm.

12. An apparatus according to claim 1, wherein said plate components are of miniaturized size and are made of glass, plastic, or metal.

13. An apparatus according to claim 1, wherein said plate components are of a size comparable to electronic chips, and are made of monocrystalline material.

* * * * *